United States Patent
Sturla et al.

(10) Patent No.: US 10,071,048 B2
(45) Date of Patent: Sep. 11, 2018

(54) COMPOSITION FOR CARING FOR KERATIN FIBERS AND USE THEREOF FOR CLEANSING AND CONDITIONING THE KERATIN FIBERS

(71) Applicant: L'OREAL, Paris (FR)

(72) Inventors: Jean-Michel Sturla, Saint-Ouen (FR); Haidong Jia, Shanghai (CN); Francoise Pataut, Saint-Ouen (FR); Roy Dhimoy, Mumbai (IN); Maxime De Boni, Mumbai (IN); Shuzo Ando, Takatsu-Ku (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/654,955

(22) PCT Filed: Dec. 27, 2012

(86) PCT No.: PCT/CN2012/087664
§ 371 (c)(1),
(2) Date: Jun. 23, 2015

(87) PCT Pub. No.: WO2014/101045
PCT Pub. Date: Jul. 3, 2014

(65) Prior Publication Data
US 2015/0328134 A1 Nov. 19, 2015

(51) Int. Cl.
| | | |
|---|---|---|
| *C11D 1/02* | (2006.01) | |
| *C11D 1/88* | (2006.01) | |
| *C11D 1/94* | (2006.01) | |
| *C11D 3/37* | (2006.01) | |
| *A61K 8/898* | (2006.01) | |
| *A61K 8/891* | (2006.01) | |
| *C11D 3/30* | (2006.01) | |
| *C11D 3/16* | (2006.01) | |
| *A61Q 5/02* | (2006.01) | |
| *A61K 8/44* | (2006.01) | |
| *A61K 8/46* | (2006.01) | |
| *A61Q 5/12* | (2006.01) | |
| *A61K 8/81* | (2006.01) | |

(52) U.S. Cl.
CPC ............. *A61K 8/898* (2013.01); *A61K 8/44* (2013.01); *A61K 8/463* (2013.01); *A61K 8/817* (2013.01); *A61K 8/891* (2013.01); *A61Q 5/02* (2013.01); *A61Q 5/12* (2013.01); *C11D 1/02* (2013.01); *C11D 1/88* (2013.01); *C11D 1/94* (2013.01); *C11D 3/162* (2013.01); *C11D 3/30* (2013.01); *C11D 3/3776* (2013.01); *A61K 2800/5426* (2013.01); *A61K 2800/596* (2013.01)

(58) Field of Classification Search
CPC ..... C11D 1/02; C11D 1/88; C11D 1/94; C11D 3/162; C11D 3/3776; C11D 3/30
USPC ........ 510/122, 123, 124, 127, 130, 136, 137, 510/138, 466, 475, 504
See application file for complete search history.

(56) References Cited

U.S. PATENT DOCUMENTS

| | | | | |
|---|---|---|---|---|
| 4,785,067 | A | * | 11/1988 | Brumbill .............. C09D 183/08 106/287.11 |
| 2003/0108503 | A1 | | 6/2003 | Maubru et al. |
| 2003/0147842 | A1 | | 8/2003 | Restle et al. |
| 2005/0100523 | A1 | | 5/2005 | Maubru et al. |
| 2006/0275245 | A1 | | 12/2006 | Decoster et al. |
| 2007/0269398 | A1 | | 11/2007 | Terada |
| 2009/0048132 | A1 | | 2/2009 | Paul et al. |
| 2015/0190334 | A1 | | 7/2015 | Somboon et al. |

FOREIGN PATENT DOCUMENTS

| | | |
|---|---|---|
| CN | 101411676 A | 4/2009 |
| EP | 2 011 477 A1 | 1/2009 |
| JP | 2000-510480 A | 8/2000 |
| JP | 2003-137722 A | 5/2003 |
| JP | 2003-206218 A | 7/2003 |
| JP | 2007-45726 A | 2/2007 |
| JP | 2008-1684 A | 1/2008 |
| JP | 2009-84525 A | 4/2009 |
| JP | 2009-534395 A | 9/2009 |
| WO | WO 98/44897 A1 | 10/1998 |
| WO | WO 2007/136708 A2 | 11/2007 |
| WO | WO 2014/023440 A1 | 2/2014 |

OTHER PUBLICATIONS

International Search Report dated Oct. 17, 2013, in PCT/CN2012/087664, filed Dec. 27, 2012.
Extended European Search Report dated Jun. 2, 2016 in Patent Application No. 12891073.4.
"Absolut Repair Shampoo", MINTEL, Database accession No. 10239042, XP-002757396, 2005, pp. 1-2.
Combined Chinese Office Action and Search Report dated Nov. 2, 2016 in Patent Application No. 201280078237.0 (with English translation of Categories of Cited Documents).
Japanese Office Action dated Nov. 14, 2016 in Patent Application No. 2015-549919 (with English language translation).

* cited by examiner

*Primary Examiner* — Gregory R Delcotto
(74) *Attorney, Agent, or Firm* — Oblon, McClelland, Maier & Neustadt, L.L.P.

(57) ABSTRACT

Composition for caring for keratin fibers and use thereof for cleansing and conditioning the keratin fibers, especially the hair, which includes A) a combination of an anionic surfactant and an amphoteric surfactant; B) at least one cationic polymer with a charge density greater than 4 meq/g; C) at least one aminated silicone; and D) at least one insoluble, non-aminated silicone.

11 Claims, No Drawings

COMPOSITION FOR CARING FOR KERATIN FIBERS AND USE THEREOF FOR CLEANSING AND CONDITIONING THE KERATIN FIBERS

FIELD OF THE INVENTION

The present invention relates to hair care cosmetic field, more specifically, it relates to new compositions having improved cleansing and conditioning properties.

BACKGROUND OF THE INVENTION

It is known to the art to use detergent and conditioning hair care composition, or shampoos, based essentially on surfactants, in particular of the anionic, nonionic and/or amphoteric type, and more especially of anionic surfactants, in combination with conditioning agents.

The surfactants, especially of anionic type for cleansing and washing the hair are known for the ability of removing the various kinds of soil initially present on the hair, and thus possess good washing power. However, along with this property, the surfactants may bring to the hair damages due to the aggressive nature of such a cleansing treatment, which leading to the pronounced damage to the hair, such as progressive removal of the lipids or proteins contained in or at the surface of the hair.

In order to improve the cosmetic properties of the above detergent composition, and more especially detergent compositions for application to sensitized hair, i.e., hair which is damaged or weakened, in particular through the chemical action of environmental agents and/or of hair treatments such as permanent-waving, dyeing or bleaching, it is known to introduce into these compositions conditioning agents. The main purpose of these conditioning agents is to rectify or limit the undesirable effects induced by the various treatments or types of attach to which the hair fibres are more or less repeatedly subjected to and, of course, they can also improve the cosmetic behavior of natural hair.

The conditioning agents most commonly used to date in shampoos are cationic polymers, silicones and/or silicone derivatives which impart to washed, dry or wet hair an disentangling, softness and a smoothness which are markedly enhanced in comparison to what can be obtained with corresponding cleansing compositions which do not contain them.

Moreover, it is also known to combine more than one conditioning agents in shampoos to obtain even better conditioning effect to the hair, especially to the sensitized hair. Different types of silicones and its derivatives are most commonly combined to achieve this purpose.

It has been found that, in spite of the current progress in the field of shampoos based on a combination of particularly and appropriately selected types of silicones and/or its derivatives and cationic polymers, they are not completely satisfactory. Thus there is still a need for new products displaying improved performance in respect to one or more of the cosmetic properties mentioned above.

The present invention is directed towards meeting this need.

SUMMARY OF THE INVENTION

One of the aims of the present invention is to obtain a composition for cleansing and at the same time conditioning keratin fibers, especially the hair, which possess a noteworthy treatment effect which manifests itself, in particular, in disentangling as well as in providing volume, bounce, smoothness, softness, and suppleness, and moreover in providing volume of foam.

The aim of the present invention is achieved by a composition for hair care, comprising, in a aqueous medium, A) at least one surfactant selected from the group consisting of anionic, nonionic, amphoteric, cationic surfactant, or a mixture thereof; B) at least one cationic polymer with a charge density greater than 4 meq/g, preferably greater than 5 meq/g; C) at least one aminated silicone; and D) at least one insoluble, non-aminated silicone.

Another subject of the present invention is a process for washing and conditioning keratin fibers, especially the hair, comprising the steps of applying to said fibers in a wet state an effective amount of the above composition, and then rinsing with water after an optional period of exposure.

Yet another subject of the present invention is the use of the above composition in cleansing and conditioning keratin fibers, especially hair.

Thus, the invention makes it possible to obtain a composition with good cleansing and conditioning properties, and meanwhile stable over time. Such properties are, namely, improved volume of foaming, better in disentangling as well as in providing volume, of bounce, smoothness, softness, and suppleness.

In the description, the terms "at least a" or "at least one" are equivalent to "one or more".

Other characteristics and advantages of the invention will emerge more clearly on reading the description and the examples that follow.

DETAILED DESCRIPTION OF THE INVENTION

As stated above, the essential components of the composition according to the invention, are A) at least one surfactant selected from the group consisting of anionic, nonionic, amphoteric, cationic surfactant, or a mixture thereof; B) at least one cationic polymer with a charge density greater than 4 meq/g, preferably greater than 5 meq/g; C) at least one aminated silicone; and D) at least one insoluble, non-aminated silicone.

A) Surfactants

The hair shampoo composition according to the invention comprises surfactants, selected from the group consisting of cationic, anionic, nonionic, amphoteric surfactant, or a mixture thereof.

i) Anionic Surfactant

According to an embodiment of the invention the at least surfactant is chosen from the anionic surfactant or "surface-active agent".

Anionic surfactant agent is understood to mean an amphiphilic compound in which the hydrophobic part carries an anionic hydrophilic group with a cationic counterion which is generally metallic (alkali metal, such as Na or K) or ammonium; the hydrophilic group is thus polar and capable of dissociating to give anions in aqueous solution.

More particularly the anionic part of the anionic surfactant is belonging to the group chosen from: $C(O)OH$, $-C(O)O^-$, $-SO_3H$, $-S(O)_2O^-$, $-OS(O)_2OH$, $-OS(O)_2O^-$, $-P(O)OH_2$, $-P(O)_2O^-$, $-P(O)O_2-$, $-P(OH)_2$, $=P(O)OH$, $-P(OH)O^-$, $=P(O)O^-$, $=POH$, $=PO^-$, the anionic part comprising a cationic counter anion such as alkali or alkaline earth metal or organic cationic counter anion such as ammonium.

Mention may be made, as anionic surface-active agents, of surface-active agents comprising carboxylate, sulfate, sulfonate, sulfoacetate, sulfosuccinate, phosphate, isethionate, sarcosinate, glutamate, lactylate or taurate anionic groups, salts of fatty acids, salts of galactosiduronic acids, salts of ether carboxylic acids and their mixtures.

More particularly, the anionic surface-active agent or agents according to the invention are chosen from:
- ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates or monoglyceride sulfates;
- ($C_6$-$C_{30}$)alkyl sulfonates, ($C_6$-$C_{30}$)alkylamidesulfonates, ($C_6$-$C_{30}$)alkylaryl sulfonates, α-olefin sulfonates, paraffin sulfonates;
- ($C_6$-$C_{30}$)akyl phosphates;
- ($C_6$-$C_{30}$)alkyl sulfosuccinates, ($C_6$-$C_{30}$)alkyl ether sulfosuccinates or ($C_6$-$C_{30}$)alkylamido sulfosuccinates;
- ($C_6$-$C_{30}$)alkyl sulfoacetates;
- ($C_6$-$C_{24}$)acylsarcosinates;
- ($C_6$-$C_{24}$)acylglutamates;
- ($C_6$-$C_{30}$)alkylpolyglycoside carboxylic ethers; ($C_6$-$C_{30}$) alkylpolyglycoside sulfosuccinates;
- ($C_6$-$C_{30}$)alkyl sulfosuccinamates;
- ($C_6$-$C_{24}$)acyl isethionates;
- N—[($C_6$-$C_{24}$)acyl]taurates;
- salts of fatty acids;
- ($C_8$-$C_{20}$)acyl lactylates;
- salts of ($C_6$-$C_{30}$)alkyl-D-galactosiduronic acids;
- salts of ($C_6$-$C_{30}$)alkyl polyoxyalkylenated ether carboxylic acids, of ($C_6$-$C_{30}$)alkylaryl polyoxyalkylenated ether carboxylic acids or of ($C_6$-$C_{30}$)alkylamido polyoxyalkylenated ether carboxylic acids;
- and their mixtures.

These anionic surface-active agents are advantageously found in the form of salts in the composition according to the invention, in particular of salts of alkali metals, such as sodium; of alkaline earth metals, such as, for example, magnesium; of ammonium salts; of amine salts; or of aminoalcohol salts. They might also, according to the conditions, occur in their acid form.

It should be noted that the alkyl or acyl radicals of these various compounds preferably comprise from 12 to 20 carbon atoms. Preferably, the aryl radical denotes a phenyl or benzyl group.

Furthermore, the polyoxyalkylenated anionic surface-active agents preferably comprise from 2 to 50 alkylene oxide groups, in particular ethylene oxide groups, or sulfates.

In accordance with a preferred embodiment of the invention, the anionic surface-active agent is chosen from salts of fatty acids.

Preferably, the anionic surfactants of the invention are sulfates, more specifically is chosen from ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates and monoglyceride sulfates, their salts such as alkali salts, such as sodium, and their mixtures.

More preferably the anionic surfactants of the invention are chosen from ($C_6$-$C_{30}$)alkyl sulfates, ($C_6$-$C_{30}$)alkyl ether sulfates, particularly ($C_6$-$C_{30}$)alkyl ether sulfates such as lauryl ether sulfate, their salts, such as sodium laureth sulfate.

ii) Nonionic Surfactant

According to an embodiment of the invention the at least surfactant is chosen from the nonionic surfactants.

Among the nonionic surfactants according to the invention, mention may be made, alone or as mixtures, of fatty alcohols, α-diols and alkylphenols, these three types of compound being oxyalkylated such as polyethoxylated, polypropoxylated and/or polyglycerolated and containing a fatty chain comprising, for example, 6 to 40 carbon atoms, the number of alkylene oxide such as ethylene oxide or propylene oxide groups possibly ranging especially from 2 to 50 and/or the number of glycerol groups possibly ranging especially from 2 to 30. Mention may also be made of copolymers of ethylene oxide and propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4 glycerol groups, ethoxylated fatty acid esters of sorbitan containing from 2 to 30 mol of ethylene oxide, fatty acid esters of sucrose, fatty acid esters of polyethylene glycol, alkylpolyglycosides, N-alkylglucamine derivatives, amine oxides such as (C10-C14)alkylamine oxides or N-acylaminopropylmorpholine oxides.

Preferably the nonionic surfactant is chosen from:
- (poly)ethoxylated fatty alcohols;
- glycerolated fatty alcohols;
- alkylpolyglycosides.

wherein "fatty chain" means a linear or branched, saturated or unsaturated hydrocarbon-based chain comprising from 6 to 30 carbon atoms and preferably from 8 to 30 carbon atoms.

As regards the alkyl polyglycosides or APGs, these compounds are well known to a person skilled in the art.

These compounds are represented more particularly by the following general formula:

$$R_1O\!-\!(R_2O)_a\!-\!(G)_b \qquad (I)$$

in which formula (I):
- $R_1$ represents a saturated or unsaturated, and linear or branched alkyl and/or alkenyl radical comprising from 8 to 24 carbon atoms or an alkylphenyl radical, wherein the linear or branched alkyl radical of which comprises from 8 to 24 carbon atoms;
- $R_2$ represents an alkylene radical comprising approximately from 2 to 4 carbon atoms;
- G represents a sugar unit comprising from 5 to 6 carbon atoms;
- a denotes a value ranging from 0 to 10 and preferably from 0 to 4, and
- b denotes a value ranging from 1 to 15.

Preferred alkyl polyglycosides useful in the composition of the present invention are compounds of formula (I) in which $R_1$ more particularly denotes a saturated or unsaturated and linear or branched alkyl radical comprising from 8 to 18 carbon atoms, a denotes a value ranging from 0 to 3 and more particularly still equal to 0, and G can denote glucose, fructose or galactose, preferably glucose.

The degree of polymerization, i.e. the value of b in the formula (I), can range from 1 to 15 and preferably from 1 to 4. The average degree of polymerization is more particularly between 1 and 2 and even more preferentially from 1.1 to 1.5.

The glycoside bonds between the sugar units are of 1-6 or 1-4 type and preferably of 1-4 type.

Compounds of formula (I) are represented in particular by the products sold by Cognis under the names Plantaren® (600 CS/U, 1200 and 2000) or Plantacare® (818, 1200 and 2000). Use may also be made of the products sold by Seppic under the names Triton CG 110 (or Oramix CG 110) and Triton CG 312 (or Oramix® NS 10), the products sold by BASF under the name Lutensol GD 70 or the products sold by Chem Y under the name AG10 LK.

Use may also be made, for example, of $C_8$-$C_{15}$ alkyl 1,4-polyglucoside as a 53% aqueous solution, sold by Cognis under the reference Plantacare® 818 UP.

As regards the mono- or polyglycerolated surfactants, they preferably comprise on average from 1 to 30 glycerol groups, more particularly from 1 to 10 glycerol groups and in particular from 1.5 to 5.

The monoglycerolated or polyglycerolated surfactants are preferably chosen from the compounds of the following formulae:

RO[CH$_2$CH(CH$_2$OH)O]$_m$H,

RO[CH$_2$CH(OH)CH$_2$O]$_m$H or

RO[CH(CH$_2$OH)CH$_2$O]$_m$H;

in which formulae:
R represents a saturated or unsaturated, linear or branched hydrocarbon-based radical comprising from 8 to 40 carbon atoms and preferably from 10 to 30 carbon atoms; m is an integer between 1 and 30, preferably between 1 and 10 and more particularly from 1.5 to 6; R may optionally comprise heteroatoms, for instance oxygen and nitrogen. In particular, R may optionally comprise one or more hydroxyl and/or ether and/or amide groups. R preferably denotes mono- or polyhydroxylated $C_{10}$-$C_{20}$ alkyl, and/or alkenyl radicals.

Use may be made, for example, of the polyglycerolated (3.5 mol) hydroxylauryl ether sold under the name Chimexane® NF from Chimex.

The (poly)ethoxylated fatty alcohols that are suitable for performing the invention are chosen more particularly from alcohols containing from 8 to 30 carbon atoms, and preferably from 12 to 22 carbon atoms.

The (poly)ethoxylated fatty alcohols more particularly contain one or more linear or branched, saturated or unsaturated hydrocarbon-based groups, comprising 8 to 30 carbon atoms, which are optionally substituted, in particular with one or more (in particular 1 to 4) hydroxyl groups. If they are unsaturated, these compounds may comprise one to three conjugated or non-conjugated carbon-carbon double bonds.

The (poly)ethoxylated fatty alcohol(s) preferably have the following formula (II):

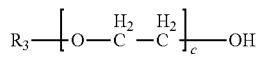

(II)

with
$R_3$ representing a linear or branched $C_8$-$C_{40}$ alkyl or alenyl group and preferably $C_8$-$C_{30}$ alkyl or alkenyl group, optionally substituted with one or more hydroxyl groups, and
c is an integer between 1 and 200 inclusive, preferentially between 2 and 50 and more particularly between 8 and 30, such as 20.

The (poly)ethoxylated fatty alcohols are more particularly fatty alcohols comprising from 8 to 22 carbon atoms, oxyethylenated with 1 to 30 mol of ethylene oxide (1 to 30 OE). Among these, mention may be made more particularly of lauryl alcohol 2 OE, lauryl alcohol 3 OE, decyl alcohol 3 OE, decyl alcohol 5 OE and oleyl alcohol 20 OE.

Mixtures of these (poly)oxyethylenated fatty alcohols may also be used.

Among the nonionic surfactants, use is preferably made of $C_6$-$C_{24}$ alkyl polyglucosides and (poly)ethoxylated fatty alcohols, $C_6$-$C_{16}$ alkyl polyglucosides are more particularly used.

iii) Amphoteric Surfactant

According to an embodiment of the invention the at least one surfactant is chosen from the amphoteric surfactants.

The amphoteric or zwitterionic surfactant(s) that may be used in the present invention may be quaternized secondary or tertiary aliphatic amine derivatives containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of ($C_8$-$C_{20}$)alkylbetaines, sulfobetaines, ($C_8$-$C_{20}$ alkyl)amido($C_2$-$C_8$ alkyl)betaines and ($C_8$-$C_{20}$ alkyl)amido($C_2$-$C_8$ alkyl)sulfobetaines.

Among the optionally quaternized secondary or tertiary aliphatic amine derivatives that may be used, as defined above, mention may also be made of the compounds of respective structures (III) and (IV) below:

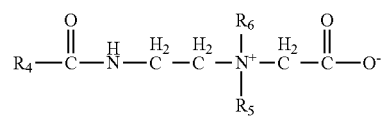

(III)

in which formula (III):
$R_4$ represents a $C_{10}$-$C_{30}$ alkyl or alkenyl group derived from an acid $R_4$—C(O)—OH preferably present in hydrolysed coconut oil, or a heptyl, nonyl or undecyl group;
$R_5$ represents a β-hydroxyethyl group; and
$R_6$ represents a carboxymethyl group;
and

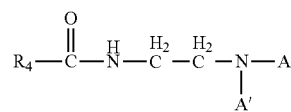

(IV)

wherein:
A represents —CH$_2$CH$_2$OX';
A' represents —(CH$_2$)z-Y', with z=1 or 2;
X' represents the group —CH$_2$—C(O)—OH, —CH$_2$—C(O)—OZ', —CH$_2$CH$_2$—C(O)—OH, —CH$_2$—CH$_2$—C(O)—OZ', or a hydrogen atom;
Y' represents —C(O)—OH, —C(O)—OZ' or the group —CH$_2$—CH(OH)—SO$_3$H or —CH$_2$—CH(OH)—SO$_3$Z';
Z' represents an ion derived from an alkali or alkaline-earth metal, such as sodium, potassium or magnesium; an ammonium ion; or an ion derived from an organic amine and in particular from an aminoalcohol, such as mono-, di- and triethanolamine, mono-, di- or triisopropanolamine, 2-amino-2-methyl-1-propanol, 2-amino-2-methyl-1,3-propanediol and tris(hydroxymethyl)aminomethane.
$R_7$ represents a $C_{10}$-$C_{30}$ alkyl or alkenyl group of an acid $R_7$C(O)—OH preferably present in coconut oil or in hydrolysed linseed oil, an alkyl group, especially of $C_{17}$ and its iso form, or an unsaturated $C_{17}$ group.

The compounds corresponding to formula (IV) are preferred. These compounds are also classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, cocoamphodipropionic acid.

By way of example, mention may be made of the N-cocoylamidocarboxymethyl glycinate of an alkali metal such as sodium, or cocoamphodiacetate sold for example by the company Rhodia under the trade name Miranol® C2M concentrate.

Among all the amphoteric or zwitterionic surfactants iii) mentioned above, use is preferably made of cocoylamidopropylbetaine, cocoylbetaine and the N-cocoylamidocarboxymethyl glycinate of an alkali metal such as sodium.

According to one specific embodiment of the present invention, the amphoteric surfactant iii) mentioned above is cocoylbetaine.

i) Cationic Surfactant;

According to an embodiment of the invention the at least surfactant is chosen from cationic surfactants. Mention may be made, for example, of optionally polyoxyalkylenated primary, secondary or tertiary fatty amine salts, quaternary ammonium salts, and mixtures thereof.

Examples of quaternary ammonium salts that may especially be mentioned include:

a) those corresponding to the general formula (V) below:

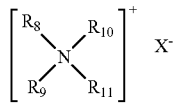

in which formula (V) the groups $R_8$ to $R_{11}$, which may be identical or different, represent a linear or branched aliphatic group comprising from 1 to 30 carbon atoms or an aromatic group such as aryl or alkylaryl, at least one of the groups $R_2$ to $R_{11}$ comprising from 8 to 30 carbon atoms and preferably from 12 to 24 carbon atoms. The aliphatic groups may comprise heteroatoms such as, in particular, oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkylacetate, $C_1$-$C_{30}$ hydroxyalkyl, $X^-$ is an anionic counterion chosen from halides, phosphates, lactates, ($C_1$-$C_4$)alkyl sulfates, and ($C_1$-$C_4$)alkyl- or ($C_1$-$C_4$) alkylarylsulfonates.

Among the quaternary ammonium salts of formula (V), preference is given firstly to tetraalkylammonium halides such as tetraalkylammonium chlorides, for instance tetraalkylammonium or alkyltrimethylammonium halides such as dialkyldimethylammonium or alkyltrimethylammonium chlorides in which the alkyl group contains from approximately 12 to 22 carbon atoms, in particular halides such as behenyltrimethylammonium chloride, distearyldimethylammonium chloride, cetyltrimethylammonium chloride, benzyldimethylstearylammonium chloride, or else, secondly, alkoxy sulfates, especially distearoylethylhydroxyethylammonium methosulfate, dipalmitoylethylhydroxyethylammonium methosulfate or distearoylethylhydroxyethylammonium methosulfate, or else, lastly, palmitylamidopropyltrimethylammonium halide, particularly the chloride or stearamidopropyldimethyl(myristyl acetate)ammonium chloride, sold under the name Ceraphyl® 70 by the company Van Dyk;

b) quaternary ammonium salts of imidazoline, for instance those of formula (VI) below:

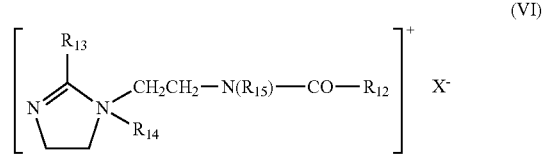

in which formula (VI):
$R_{12}$ represents an alkenyl or alkyl group comprising from 8 to 30 carbon atoms, for example fatty acid derivatives of tallow;
$R_{13}$ represents a hydrogen atom, a $C_1$-$C_4$ alkyl group or an alkenyl or alkyl group comprising from 8 to 30 carbon atoms;
$R_{14}$ represents a $C_1$-$C_4$ alkyl group;
$R_{15}$ represents a hydrogen atom or a $C_1$-$C_4$ alkyl group;
X represents an anionic counterion chosen in particular from halides, phosphates, acetates, lactates, ($C_1$-$C_4$) alkyl sulfates, ($C_1$-$C_4$)alkyl- or ($C_1$-$C_4$)alkylarylsulfonates.
$R_{12}$ and $R_{13}$ preferably denote a mixture of alkyl or alkenyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

c) quaternary diammonium or triammonium salts, particularly of formula (VII) below:

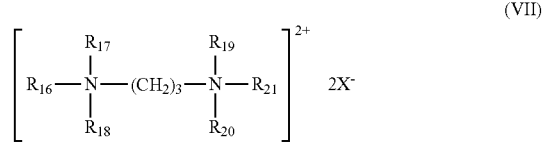

in which formula (VII):
$R_{16}$ denotes an alkyl group comprising from about 16 to 30 carbon atoms, which is optionally hydroxylated and/or interrupted with one or more oxygen atoms;
$R_{17}$ is chosen from hydrogen, an alkyl group comprising from 1 to 4 carbon atoms or a group —($CH_2$)$_3$—$N^+$ ($R_{16a}$)($R_{17a}$)($R_{18a}$); $R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms, and
$X^-$ represents an anionic counterion chosen in particular from halides, acetates, phosphates, nitrates, ($C_1$-$C_4$) alkyl sulfates, ($C_1$-$C_4$)alkyl- or ($C_1$-$C_4$)alkylarylsulfonates, in particular methyl sulfate and ethyl sulfate. Such compounds are, for example, Finquat CT-P, available from the company Finetex (Quaternium 89), and Finquat CT, available from the company Finetex (Quaternium 75);

d) quaternary ammonium salts containing one or more ester functions, such as those of formula (VIII) below:

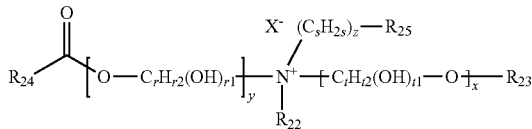
(VIII)

in which formula (VIII):
R$_{22}$ is chosen from C$_1$-C$_6$ alkyl and C$_1$-C$_6$ hydroxyalkyl or dihydroxyalkyl groups;
R$_{23}$ is chosen from:
the group

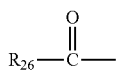

linear or branched, saturated or unsaturated C$_1$-C$_{22}$ hydrocarbon-based groups R$_{27}$,
a hydrogen atom;
R$_{25}$ is chosen from:
the group

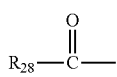

linear or branched, saturated or unsaturated C$_1$-C$_6$ hydrocarbon-based groups R$_{29}$,
a hydrogen atom;
R$_{24}$, R$_{26}$ and R$_{28}$, which may be identical or different, are chosen from linear or branched, saturated or unsaturated C$_7$-C$_{21}$ hydrocarbon-based groups;
r, s and t, which may be identical or different, are integers ranging from 2 to 6;
r1 and t1, which may be identical or different, are equal to 0 or 1, with r2+r1=2r and t1+t2=2t,
y is an integer ranging from 1 to 10;
x and z, which may be identical or different, are integers ranging from 0 to 10;
X$^-$ represents an organic or inorganic anionic counterion;
with the proviso that the sum x+y+z is from 1 to 15, that when x is 0, then R$_{23}$ denotes R$_{27}$ and that when z is 0, then R$_{25}$ denotes R$_{29}$.

The alkyl groups R$_{22}$ may be linear or branched, and more particularly linear.

Preferably, R$_{22}$ denotes a methyl, ethyl, hydroxyethyl or dihydroxypropyl group, and more particularly a methyl or ethyl group.

Advantageously, the sum x+y+z is from 1 to 10.

When R$_{23}$ is a hydrocarbon-based group R$_{27}$, it may be long and may contain from 12 to 22 carbon atoms, or may be short and may contain from 1 to 3 carbon atoms.

When R$_{25}$ is a hydrocarbon-based group R$_{29}$, it preferably contains 1 to 3 carbon atoms.

Advantageously, R$_{24}$, R$_{26}$ and R$_{28}$, which may be identical or different, are chosen from linear or branched, saturated or unsaturated C$_{11}$-C$_{21}$ hydrocarbon-based groups, and more particularly from linear or branched, saturated or unsaturated C$_{11}$-C$_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion X$^-$ is preferably a halide, preferably such as chloride, bromide or iodide, a (C$_1$-C$_4$)alkyl sulfate or a (C$_1$-C$_4$)alkyl- or (C$_1$-C$_4$)alkylaryl-sulfonate. However, use may be made of methanesulfonate, phosphate, nitrate, tosylate, an anion derived from an organic acid, such as acetate or lactate, or any other anion compatible with the ammonium containing an ester function.

The anionic counterion X$^-$ is even more particularly chloride, methyl sulfate or ethyl sulfate.

Use is made more particularly, in the composition according to the invention, of the ammonium salts of formula (VIII) in which:
R$_{22}$ denotes a methyl or ethyl group,
x and y are equal to 1,
z is equal to 0 or 1,
r, s and t are equal to 2,
R$_{23}$ is chosen from:
the group

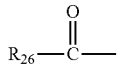

methyl, ethyl or C14-C22 hydrocarbon-based groups,
a hydrogen atom,
R$_{25}$ is chosen from:
the group

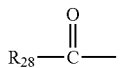

a hydrogen atom,
R$_{24}$, R$_{26}$ and R$_{28}$, which may be identical or different, are chosen from linear or branched, saturated or unsaturated C$_{13}$-C$_{17}$ hydrocarbon-based groups, and more particularly from linear or branched, saturated or unsaturated C$_{13}$-C$_{17}$ alkyl and alkenyl groups.

Advantageously, the hydrocarbon-based radicals are linear.

Among the quaternary ammonium salts containing one or more ester functions of formula (VIII), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of mono-, di- and triesters with a weight majority of diester salts.

It is also possible to use the ammonium salts containing at least one ester function that are described in U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylammonium salts, and mixtures thereof, and more particularly behenyltrimethylammonium chloride, cetyltrimethylammonium chloride, and dipalmitoylethylhydroxyethylammonium methosulfate, and mixtures thereof. Preferably, the surfactant is selected from anionic surfactant and amphoteric surfactant. Based on this particular embodiment, the surfactant useful n the invention is a combination of anionic surfactant and emphoteric surfactant.

More preferably, the surfactant of the invention contains a combination of a sulfate anionic surfactant and a betaine surfactant, preferably sodium laureth sulfate and cocoyl-betain.

Advantageously, the content of at least one surfactant represents from 4% to 50% by weight, with respect to the weight of the composition, preferably from 6% to 40% by weight, more preferably from 10% to 20% by weight, even more preferably from 12% to 16% by weight with respect to the weight of the composition.

B) Cationic Polymer with a Charge Density Greater than 4 meq/g

The hair shampoo composition according to the present invention, comprising at least one cationic polymer with a charge density greater than 4 meq/g, preferably greater than 5 meq/g.

It is first recalled that, for the purposes of the present invention, the term "cationic polymer" denotes any polymer containing cationic groups and/or groups that can be ionized into cationic groups.

In view of the present invention, the charge density of the cationic polymers according to the invention is greater than 4 meq./g and even more preferentially greater than 5 meq./g.

This charge density is especially determined by the Kjeldahl method.

It may also be calculated from the chemical nature of the polymer.

These polymers preferably have a number-average molecular mass generally of between 1,000 and 100,000,000.

Polymers of this type are especially described in FR 2 320 330, FR 2 270 846, FR 2 316 271, FR 2 336 434, FR 2 413 907, U.S. Pat. Nos. 2,273,780, 2,375,853, 2,388,614, 2,454, 547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

More particularly, the cationic polymer(s) are chosen from:

a) Cationic cyclopolymer alkyldiallylamine or dialkyldiallylammonium

The said cationic cyclopolymer may be a homopolymer or copolymer containing, as main constituent of the chain, units corresponding to formula (IX) or (X):

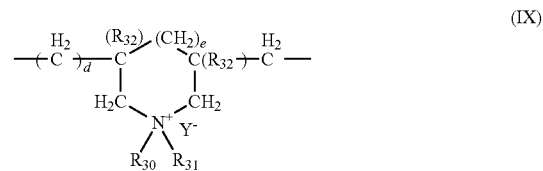

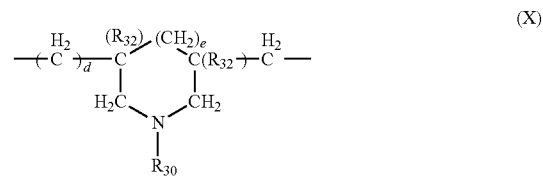

in which formula d and e are equal to 0 or 1, the sum d+e being equal to 1; $R_{32}$ denotes a hydrogen atom or a methyl radical; $R_{30}$ and $R_{31}$, independently of each other, denote a $C_1$-$C_8$ alkyl group, a hydroxyalkyl group in which the alkyl group is $C_1$-$C_5$, an amidoalkyl group in which the alkyl is $C_1$-$C_4$; $R_{30}$ and $R_{31}$ can also denote, together with the nitrogen atom to which they are attached, a heterocyclic group such as piperidyl or morpholinyl; $R_{30}$ and $R_{31}$, independently of each other, preferably denote a $C_1$-$C_4$ alkyl group; $Y^-$ is an organic or mineral anion such as bromide, chloride, acetate, borate, citrate, tartrate, bisulfate, bisulfite, sulfate or phosphate. These polymers are described in particular in FR 2 080 759 and FR 2 190 406.

The cationic cyclopolymer of the present invention is a water soluble polymer having a charge density greater than 4 meq/g. From the viewpoints of smoothness during foaming and smoothness during rinsing, the charge density is preferably greater than 5 meq/g. The charge density of the water soluble cationic cyclopolymer may be measured by the colloid titration method using, for example, potassium polyvinylsulfate as a titration solution.

Among the polymers defined above, mention may be made more particularly of the dimethyldiallylammonium chloride homopolymer sold under the name "Merquat 100" by the company Nalco (and its homologues of low weight-average molecular mass) and the copolymers of diallyldimethylammonium chloride and of acrylamide, sold under the name Merquat 550.

b) Polyquaternary ammonium polymers consisting of units of formula (XI):

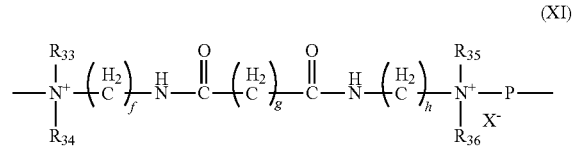

in which formula:

$R_{33}$, $R_{34}$, $R_{35}$ and $R_{36}$, which may be identical or different, represent a hydrogen atom or a methyl, ethyl, propyl, b-hydroxyethyl, b-hydroxypropyl or —CH$_2$CH$_2$(OCH$_2$CH$_2$)pOH radical, where p is equal to 0 or to an integer between 1 and 6, with the proviso that $R_{33}$, $R_{34}$, $R_{35}$ and $R_{36}$ do not simultaneously represent a hydrogen atom, f and g, which may be identical or different, are integers between 1 and 6, h is equal to 0 or to an integer between 1 and 34, X$^-$ denotes an anion such as a halide, P denotes a dihalide radical or preferably represents —CH$_2$—CH$_2$—O—CH$_2$—CH$_2$—.

Such compounds are described especially in Patent application EP-A-122 324.

Among these, mention may be made, for example, of the products Mirapol® A 15, Mirapol® AD1, Mirapol® AZ1 and Mirapol® 175, sold by the company Miranol.

Advantageously, the cationic cyclopolymer used in the present invention is in presence in the composition from 0.01% to 3% by weight, preferably from 0.1% to 2%, more preferably from 0.3% to 1% by weight relative to the total weight of the composition.

C) Aminated Silicone

According to the invention, the term "aminated silicone", or amino silicone, denotes any silicone comprising at least one primary, secondary or tertiary amine or one quaternary ammonium, and more particularly at least one primary amine. Amino silicones do not comprise any quaternary ammonium groups.

The aminated silicones used in the cosmetic composition according to the present invention are chosen from the silicones of formula (XII) below:

$$(R_{37})_i(D)_{3-i}\text{-Si[Osi(D)}_2]_j\text{-[OSi(D)}_k(R_{37})_{2-k}]_l\text{—OSi(D)}_{3-i'}(R_{37})_{i'} \quad \text{(XII)}$$

in which,

D is a hydrogen atom, or a phenyl, hydroxyl (—OH), or C$_1$-C$_8$ alkyl, and preferably methyl, or C$_1$-C$_8$ alkoxy, preferably methoxy, radical, i denotes the number 0 or an integer from 1 to 3, and preferably 0, k denotes 0 or 1, and in particular 1, j and l are numbers such that the sum (j+l) can range especially from 1 to 2000 and in particular from 50 to 150, it being possible for n to denote a number from 0 to 1999 and in particular from 49 to 149, and for m to denote a number from 1 to 2000 and in particular from 1 to 10;

$R_{37}$ is a monovalent radical of formula —C$_q$H$_{2q}$L in which q is a number from 2 to 8, it being possible for one or more hydrogen atoms to be substituted with a hydroxyl group, and L is an optionally quaternized amino group chosen from the groups:

—N(R$_{38}$)—CH$_2$—CH$_2$—N(R'$_{38}$)$_2$;

—N(R$_{38}$)$_2$;

—N$^+$(R$_{38}$)$_3$Q$^-$;

—N$^+$(R$_{38}$)(H)$_2$Q$^-$;

—N$^+$(R$_{38}$)$_2$HQ$^-$;

—N(R$_{38}$)—CH$_2$—CH$_2$—N$^+$(R'$_{38}$)(H)$_2$Q$^-$;

in which R$_{38}$ and R'$_{38}$ can denote a hydrogen atom, a phenyl, a benzyl, or a monovalent saturated hydrocarbon-based radical, for example a C$_1$-C$_{20}$ alkyl radical, and Q and Q represents an anion such as, for example, fluoride, chloride, bromide or iodide.

In particular, the aminated silicones corresponding to the definition of formula (XII) are chosen from the compounds corresponding to the formula (XIII) below:

(XIII)

$$R_{39}-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_n-\left[O-\underset{\underset{\underset{\underset{\underset{NH_2}{|}}{CH_2}}{|}}{\underset{NH}{|}}}{\overset{\overset{R_{40}}{|}}{Si}}\right]_m-O-\underset{\underset{CH_3}{|}}{\overset{\overset{CH_3}{|}}{Si}}-R_{41}$$

in which $R_{39}$, $R_{40}$ and $R_{41}$, which may be identical or different, denote a C$_1$-C$_4$ alkyl radical, preferably CH$_3$; a C$_1$-C$_4$ alkoxy radical, preferably methoxy; or OH; E represents a linear or branched, C$_3$-C$_8$ and preferably C$_3$-C$_6$ alkylene radical; m and n are integers dependent on the molecular weight and the sum of which is between 1 and 2000.

According to a first possibility, $R_{39}$, $R_{40}$ and $R_{41}$, which may be identical or different, represent a C$_1$-C$_4$ alkyl radical, preferably methyl, or a hydroxyl radical, E represents a C$_1$-C$_8$ and preferably C$_3$-C$_4$ alkylene radical, and m and n are such that the weight-average molecular weight of the compound is between 5000 and 500 000 approximately. The compounds of this type are called "aminodimethicone" in the CTFA dictionary.

According to a second possibility, $R_{39}$, $R_{40}$ and $R_{41}$, which may be identical or different, represent a C$_1$-C$_4$ alkoxy or hydroxyl radical, at least one of the radicals $R_{39}$ or $R_{41}$ is an alkoxy radical and E represents a C$_3$ alkylene radical. The hydroxy/alkoxy molar ratio is preferably between 0.2/1 and 0.4/1 and advantageously equal to 0.3/1. Moreover, m and n are such that the weight-average molecular weight of the compound is between 2000 and 10$^6$. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, $R_{39}$ or $R_{41}$, which are different, represent a C$_1$-C$_4$ alkoxy or hydroxyl radical, at least one of the radicals $R_{40}$ or $R_{41}$ is an alkoxy radical, $R_{40}$ represents a methyl radical and E represents a C$_3$ alkylene radical. The hydroxy/alkoxy molar ratio is preferably between 1/0.8 and 1/1.1, and advantageously is equal to 1/0.95. Moreover, m and n are such that the weight-average molecular weight of the compound is between 2000 and 200 000. More particularly, n is between 0 and 999 and m is between 1 and 1000, the sum of n and m being between 1 and 1000.

More particularly, mention may be made of the product Fluid WR® 1300 sold by Wacker, and product Xiameter® MEM-8299 Emulsion sold by Dow Corning.

The amino silicones used in the composition in accordance with the invention preferably have general formula (XIV) below:

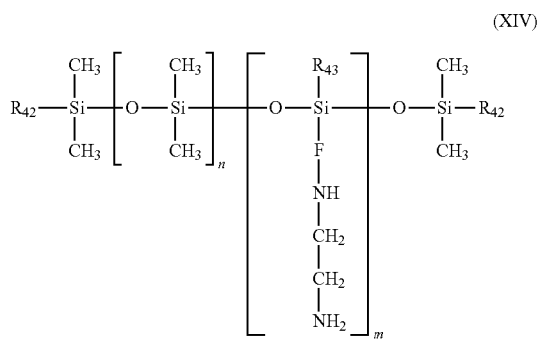

(XIV)

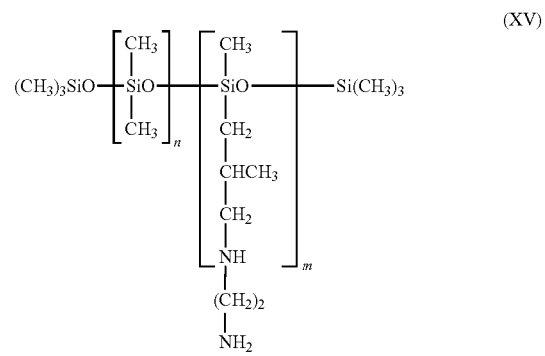

(XV)

in which:

F denotes a $C_2$-$C_8$ and preferably $C_2$-$C_6$, better still $C_3$, linear or branched alkylene radical;

$R_{42}$ and $R_{43}$ denote, independently of one another, a $C_1$-$C_4$ alkyl, preferably methyl, radical or a $C_1$-$C_4$ alkoxy, preferably methoxy, radical or a hydroxyl radical, m and n are numbers such that the weight-average molecular weight (Mw) is greater than or equal to 75 000.

Preferably, the radicals $R_{42}$ are identical and denote a hydroxyl radical.

Preferably, the viscosity of the amino silicone according to the invention is greater than 25 000 mm²/s measured at 25° C. More preferentially, the viscosity of the amino silicone is between 30 000 and 200 000 mm2/s at 25° C. and even more preferentially between 50 000 and 150 000 mm²/s, measured at 25° C., and even better still from 70 000 to 120 000 min²/s. The viscosities of the silicones are, for example, measured according to standard "ASTM 445 Appendix C".

Preferably, the cationic charge of the aminated silicone according to the invention is less than or equal to 0.5 meq/g, preferably ranging from 0.01 to 0.1 meq/g and better still from 0.03 to 0.06 meq./g.

Preferably, the amino silicone according to the invention has a weight-average molecular weight (Mw) ranging from 75 000 to 1 000 000 and even more preferentially ranging from 100 000 to 200 000.

The weight-average molecular weights of the amino silicones according to the invention are measured by gel permeation chromatography (GPC) at ambient temperature, as polystyrene equivalents. The columns used are μ styragel columns. The eluent is THF and the flow rate is 1 ml/minute. 200 μl of a solution containing 0.5% by weight of silicone in THF are injected. Detection is performed by refractometry and UV-metry.

A particularly preferred amino silicone corresponding to formula (XIV) is, for example, Dow Corning 2-8299 Cationic Emulsion from the company Dow Corning.

A product corresponding to the definition of formula (XII) is in particular the polymer called "trimethylsilylamodimethicone" in the CTFA dictionary, corresponding to formula (XV) below:

in which n and m have the meanings given above in accordance with formula (XIII).

Such compounds are described, for example, in EP 95238; a compound of formula (XIV) is, for example, sold under the name Q2-8220 by the company OSI.

Other amino silicones according to the invention are quaternized amino silicones, and in particular:

(a) the compounds corresponding to formula (XVI) below:

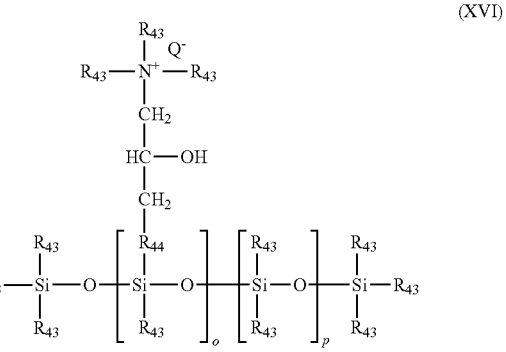

(XVI)

in which, $R_{43}$ represents a $C_1$-$C_{18}$ alkyl radical, for example methyl;
$R_{44}$ represents a divalent hydrocarbon-based radical, in particular a $C_1$-$C_{18}$ alkylene radical;
$Q^-$ is an anion, in particular chloride;
o represents a mean statistical value from 2 to 20 and in particular from 2 to 8;
p represents a mean statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56;

(b) the quaternary ammonium silicones of formula (XVII):

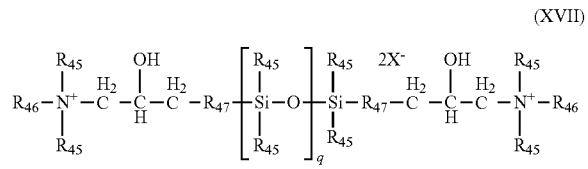

(XVII)

in which:
R$_{45}$, which may be identical or different, represent a monovalent hydrocarbon-based radical containing from 1 to 8 carbon atoms, and in particular a C$_1$-C$_8$ alkyl radical, for example methyl;
R$_{47}$ represents a divalent hydrocarbon-based radical, especially a C$_1$-C$_{18}$ alkylene radical or a divalent C$_1$-C$_{18}$, and for example C$_1$-C$_8$, alkylenoxy radical linked to the Si via an SiC bond;
R$_{46}$, which may be identical or different, represent a hydrogen atom, a monovalent hydrocarbon-based radical containing from 1 to 18 carbon atoms, and in particular a C$_1$-C$_{18}$ alkyl radical, a C$_2$-C$_{18}$ alkenyl radical or a radical —R$_{47}$—NHCOR$_{45}$;
X$^-$ is an anion such as a halide ion, especially chloride, or an organic acid salt (acetate, etc.);
r represents a mean statistical value from 2 to 200 and in particular from 5 to 100.
These silicones are, for example, described in Application EP-A-0530974;
(c) the aminated silicones of formula (XVIII):

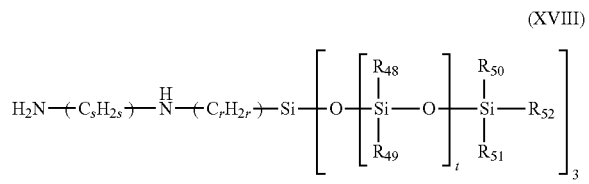

(XVIII)

in which:
R$_{48}$, R$_{49}$, R$_{50}$ and R$_{51}$, which may be identical or different, denote a C$_1$-C$_4$ alkyl radical or a phenyl group,
R$_{52}$ denotes a C$_1$-C$_4$ alkyl radical or a hydroxyl group,
r is an integer ranging from 1 to 5,
s is an integer ranging from 1 to 5,
and in which t is selected such that the amine number is between 0.01 and 1 meq/g.
Preferably, the amino silicones of the invention are non-quaternized, i.e. they do not comprise a nitrogen atom with a permanent charge.
The silicones which are particularly preferred in accordance with the invention are polysiloxanes comprising amino groups, such as amodimethicones or trimethylsilylamodimethicones, and in particular the compounds of formulae (XIII), (XIV) and (XV).
When the aminated silicones of the invention are used, a particularly advantageous embodiment is their joint use with cationic and/or nonionic surfactants.
By way of example, it is possible to use the product sold under the name Cationic Emulsion DC 929 by the company Dow Corning, which comprises, besides amodimethicone, a cationic surfactant comprising a mixture of products corresponding to the formula:

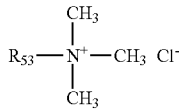

in which R$_{53}$ denotes C$_{14}$-C$_{22}$ alkenyl and/or alkyl radicals derived from tallow fatty acids, and known under the CTFA name tallowtrimonium chloride, in combination with a nonionic surfactant of formula: C$_9$H$_{19}$—C$_6$H$_4$—(OC$_2$H$_4$)$_{10}$—OH, known under the CTFA name Nonoxynol 10.
Use may also be made, for example, of the product sold under the name Cationic Emulsion DC 939 by the company Dow Corning, which comprises, besides amodimethicone, a cationic surfactant which is trimethylcetylammonium chloride and a nonionic surfactant of formula: C$_{13}$H$_{27}$—(OC$_2$H$_4$)$_{12}$—OH, known under the CTFA name Trideceth-12.
When these amino silicones are used, one particularly advantageous embodiment consists in using them in the form of an oil-in-water emulsion.
The oil-in-water emulsion may comprise one or more surfactants. The surfactants may be of any nature but are preferably cationic and/or nonionic.
The silicone particles in the emulsion have a volume-average diameter [D4.3] generally ranging from 10 nm to 1000 nanometers, preferably from 50 nm to 800 nanometers, more particularly from 100 nm to 600 nanometers and even more particularly from 200 nm to 500 nanometers. These particle sizes may be determined especially using a laser granulometer, for example the Malvern Mastersizer 2000 granulometer.
According to the invention, all the silicones can also be used in the form of emulsions or of microemulsions.
According to the invention, the aminated silicone(s) of the present invention can represent from 0.01% to 7% by weight, preferably from 0.1% to 5% by weight and more particularly from 0.4% to 2% by weight relative to the total weight of the composition.
D) Insoluble, Non-Aminated Silicone
In the context of the present invention, the term "insoluble" is understood to mean insoluble in the final composition.
In the context of the present invention, the term "silicone" is understood to mean, in conformity with the generally accepted definition, all organosilicon polymers or oligomers having a linear or cyclic, branched or crosslinked structure, of variable molecular weight, obtained by polymerization and/or polycondensation of appropriately functionalized silanes, and comprising in essence a repetition of main units in which the silicon atoms are joined to one another by oxygen atoms (siloxane link .tbd.Si—O—Si.tbd.), optionally substituted hydrocarbon radicals being linked directly via a carbon atom to the said silicon atoms. The most common hydrocarbon radicals are alkyl radicals, in particular C.sub.1-C.sub.10 alkyl radicals and especially methyl, fluoroalkyl radicals, and aryl radicals and especially phenyl.
According to the invention, the silicone of appropriate viscosity is preferably selected from:
(i) polydialkylsiloxanes;
(ii) polydiarylsiloxanes; and
(iii) polyalkylarylsiloxanes.
Among polydialkylsiloxanes, mention may preferably be made of:
linear polydimethylsiloxanes containing terminal trimethylsilyl groups, such as, for example, and without implied limitation, the SILBIONE oils of the 70047 series, marketed by RHONE-POULENC,
linear polydimethylsiloxanes containing terminal hydroxydimethylsilyl groups, such as the oils of the 48 V series from RHONE-POULENC, product Xiameter® PMX-200 silicone fluid 60000CS sold by Dow Corning, or a mixture thereof.
In this class of polydialkylsiloxanes, mention may more preferably be made of the polyalkylsiloxanes sold by the company GOLDSCHMIDT under the trade names ABIL-WAX 9800 and ABILWAX 9801, which are poly(C.sub.1-C.sub.20)alkylsiloxanes.

Among polyalkylarylsiloxanes, mention may preferably be made of linear or branched polydimethylmethylphenyl-siloxanes or polydimethyldiphenylsiloxanes, such as the product DC 556 COSMETIC GRAD FLUID from DOW CORNING.

Preferably, the insoluble non-aminated silicone according to the present invention is polydimethylsiloxanes.

Advantageously, the amount of the insoluble, non-aminated silicone of the present invention is from 0.01% to 7% by weight, preferably from 0.1% to 5% by weight, more preferably from 0.5% to 3% by weight, even more preferably from 1% to 2% relative to the total weight of the composition.

The compositions according to the invention may naturally contain, in addition, all the standard adjuvants encountered in the field of shampoos, such as, for example, perfumes, preservatives, sequestering agents, thickeners, hydrating agents, antidandruff or antiseborrhoeic agents, vitamins, sunscreen agents, suspending agents and the like.

Naturally, a person skilled in the art will take care to choose this/these possible supplementary compound(s) and/or the amounts thereof in such a way that the advantageous bination according to the invention are not, or are not substantially, impaired by the addition or additions envisaged.

The composition according to the invention may take the form of thickened liquid, creams or gel, They may also take the form of lotions to be rinsed.

Another aspect of the invention is a process for washing and conditioning keratin fibers, especially the hair, comprising the steps of applying to said fibers in a wet state an effective amount of the composition described above, and then rinsing with water after an optional period of exposure.

Yet another aspect of the present invention is the use of the above composition of the invention for cleansing and conditioning keratin fibers, especially hair.

Non limiting examples illustrating the invention are given.

EXAMPLES

Three hair shampoos were prepared, one according to the invention (Invention A) and two comparative (Comparative B and C):

| Ingredient name | % by weight of active ingredient | | |
|---|---|---|---|
| | Invention A | Comparative B | Comparative C |
| SODIUM LAURETH SULFATE 70% containing 1 mol of ethylene oxide (Sodium laureth sulfate, SLES(N1EO) from Zhejiang Zanyu Technology) | 13.5 | 13.5 | 13.5 |
| COCOYLBETAINE (Cocoylbetaine, Mirataine ® BB/FLA from Rhodia) | 2.25 | 2.25 | 2.25 |
| POLYQUATERNIUM-6 (Polydiallyl dimethyl ammonium chloride, Merquat ™ 100 polymer from Nalco (Lubrizol)) | 0.42 | | |
| POLYQUATERNIUM-10 (Cationic hydroxyethyl cellulose, Ucare ™ Polymer JR 400 LT from DOW Corning) | | 0.42 | |
| GUAR HYDROXYPROPYLTRIMONIUM CHLORIDE (Guar hydroxypropyltrimonium chloride, Jaquar C-13-S from Rhodia) | | | 0.42 |
| DIMETHICONE (Polydimethylsiloxanes, Xiameter ® PMX-200 silicone fluid 60000CS from Dow Corning) | 1.2 | 1.2 | 1.2 |
| AMODIMETHICONE (and) TRIDECETH-6 (and) CETRIMONIUM CHLORIDE (A combination of 57% amodimethicone, 5% trideceth-6, and 1% cetrimonium chloride, Xiameter ® MEM-8299 Ejulsion from Dow Corning) | 0.4 | 0.4 | 0.4 |
| CITRIC ACID qs pH | 5.2 | 5.2 | 5.2 |
| WATER | qs 100 g | qs 100 g | qs 100 g |

All the examples are evaluated using wet combing method and dry combing method.

Wet Combing after Rinsing 0.4 g of the Invention A and Comparative B, C samples was applied respectively on 1 g of bleached Chinese hair. The conditioning compositions were then left on the hair for 5 minutes. The hair are rinsed by warm water for 10 seconds. The friction force between the hair and comb is measured by the instrument named Texture Analyzer provided by Texture Technologies, Scarsdale, USA.

The combing force of the hair were listed below:

| Combing force (N) | | |
|---|---|---|
| Invention A | Comparative B | Comparative C |
| 0.59 | 1.1 | 0.91 |

The combing force of the hair used the Invention A sample had been reduced significantly, with comparison to Comparative B and C.

Dry Combing after Rinsing 0.4 g of the A and Comparative B, C samples are applied on 6 g of natural black Chinese hair and damaged Chinese hair, respectively. The conditioning composition is then left on the hair for 5 minutes. Then the hair is rinsed by warm water for 10 seconds, and left to dry over night at room temperature. After 5 times repeated application using the process described herein, the combing force between the hair stress and a comb is measured by the device named Combing Tester JC45A-001, sold by JAU CHUNG. The reduction of combing force is measured based on the following formula:

Reduction of combing force (%)=[combing force of control (9% of sodium laureth sulfate)−combing force of example)/combing force of 9% sodium laureth sulfate]×100%.

| | Reduction of dry combing force (%) | | |
|---|---|---|---|
| Attribute | Invention A | Comparative B | Comparative C |
| Natural black Chinese hair | 83 | 56 | 70 |
| Damaged Chinese hair | 78 | 48 | 68 |

The dry combing force of the hair using Invention A example has been reduced significantly.

Panel Test

Shampooing was performed by applying approximately 10 g of the compositions A, B and C to previously wetfted hair. The shampoo was worked to lather and the hair was then rinsed copiously with water.

A panel of 6 experts evaluated the disentangling of the wet hair, the ease of shaping, the softness, smoothness, and suppleness of the hair. The performances of each are sorted by level 0 to 5, whereas 0 represents bad performance, and 5 represents excellent performance. The higher the number is, the better the performance is.

The results of the evaluation were listed:

| Property | Performance | | |
|---|---|---|---|
| | Invention A | Comparative B | Comparative C |
| Disentangling of wet hair | 3.1 | 1.8 | 2.5 |
| Wet-smoothness | 4 | 2.4 | 3.4 |
| Wet-suppleness | 3.5 | 2.4 | 2.5 |
| Dry -smoothness | 3.8 | 2.4 | 2.5 |
| Dry-Suppleness | 3.5 | 2.7 | 2.5 |

Based on the evaluation made by the panels, the current invention has a remarkable improvement in all of these properties with comparison to the comparative B and C.

The invention claimed is:

1. A composition consisting of, in an aqueous phase:
   A) a combination of a single anionic surfactant and an amphoteric surfactant;
   B) a cationic polymer with a charge density greater than 4 meq/g;
   C) an aminated silicone;
   D) an insoluble, non-aminated silicone; and
   E) optionally one or more of perfume, preservative, sequestering agent, thickener, hydrating agent, antidandruff agent, antiseborrhoeic agent, vitamin, sunscreen agent, and suspending agents.

2. The composition according to claim 1, wherein the anionic surfactant and amphoteric surfactant are present in the composition in an amount of from 4% to 50% by weight-relative to a total weight of the composition.

3. The composition according to claim 1, wherein the cationic polymer is selected from the group consisting of a cationic cyclopolymer alkyldiallylamine, a cationic cyclopolymer dialkyldiallylammonium, a diquaternary ammonium cationic polymer, and a polyquaternaty ammonium polymer.

4. The composition according to claim 1, wherein the cationic polymer is a cationic cyclopolymer of alkyldiallylamine or dialkyldiallylamrnonium having a unit of formula (IX) or (X)

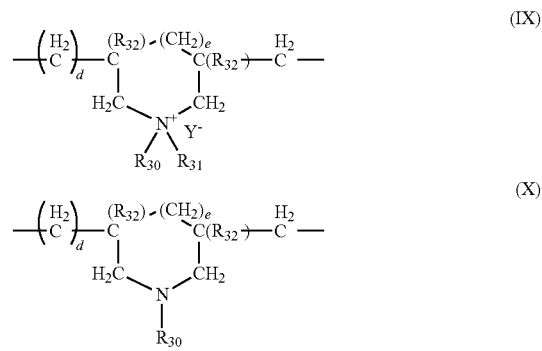

wherein:
d and e are the same or different, and are equal to 0 or 1, $d+e=1$, $R_3$ denotes a hydrogen atom or a methyl radical, $R_{30}$ and $R_{31}$ each independently denotes a $C_1$-$C_6$ alkyl group, a hydroxyalkyl group in which the alkyl group is $C_1$-$C_5$, or an amidoalkyl group in which the alkyl is $C_1$-$C_4$, and may, together with the nitrogen atom to which they are attached, form a heterocyclic group, $Y^-$ is an organic or mineral anion, wherein the cationic cyclopolymer of alkyldiallylamine or dialkyldiallylammonium having a unit of formula (IX) or (X) has a charge density greater than 4 meq/g.

5. The composition according to claim 1, wherein the cationic polymer is polydiallyl dimethyl ammonium chloride.

6. The composition according to claim 1, wherein the cationic polymer is a cationic cyclopolymer alkyldiallylamine, a cationic cyclopolymer dialkyldiallylammonium, or both, in a total amount of from 0.01% to 3% by weight relative to a total weight of the composition.

7. The composition according to claim 1, wherein the aminated silicone is a polydimethylsiloxane.

8. The composition according to claim 1, wherein the aminated silicone is present in the composition in an amount of from 0.01% to 7% by weight relative to a total weight of the composition.

9. The composition according to claim 1, wherein the insoluble, non-aminated silicone is at least one member selected from the group consisting of a polydialkylsiloxane, a polydiarylsiloxane, and a polyalkylarylsiloxane.

10. The composition according to claim 1, wherein the insoluble, non-aminated silicone is present in the composition in an amount of from 0.01% to 7% by weight relative to a total weight of the composition.

11. A process for washing and conditioning keratinous fibers, comprising applying to the fibers in a wet state an effective amount of the composition according to claim 1, and then rinsing with water after an optional period of exposure.

* * * * *

UNITED STATES PATENT AND TRADEMARK OFFICE
CERTIFICATE OF CORRECTION

PATENT NO. : 10,071,048 B2
APPLICATION NO. : 14/654955
DATED : September 11, 2018
INVENTOR(S) : Jean-Michel Sturla et al.

Page 1 of 1

It is certified that error appears in the above-identified patent and that said Letters Patent is hereby corrected as shown below:

In the Claims

Column 21, Line 52, Claim 3, delete "polyquaternaty" and insert --polyquaternary--;

Column 21, Line 56, Claim 4, delete "dialkyldiallylamrnonium" and insert --dialkyldiallylammonium--.

Column 22, Line 20, Claim 4, delete "$R_3$" and insert --$R_{32}$--.

Signed and Sealed this
Fourth Day of June, 2019

Andrei Iancu
*Director of the United States Patent and Trademark Office*